United States Patent [19]

Gillespie

[11] 4,255,416
[45] Mar. 10, 1981

[54] SKIN FIRMING COMPOSITION AND METHOD

[76] Inventor: Sally I. Gillespie, 233 N. Causeway, New Smyrna Beach, Fla. 32069

[21] Appl. No.: 67,140

[22] Filed: Aug. 16, 1979

Related U.S. Application Data

[63] Continuation-in-part of Ser. No. 22,846, Mar. 22, 1979, abandoned.

[51] Int. Cl.$^3$ .......................... A61K 7/02; A61K 7/021
[52] U.S. Cl. .......................................... 424/80; 424/63; 424/357; 424/361
[58] Field of Search ................................. 424/357, 80

[56] References Cited

U.S. PATENT DOCUMENTS

| | | | |
|---|---|---|---|
| 2,533,210 | 4/1951 | Baer | 450/611 |
| 3,016,334 | 1/1962 | Lewis | 424/359 |
| 3,341,319 | 9/1967 | Hibbard | 424/80 X |
| 3,523,998 | 8/1970 | Feinstone | 424/78 |
| 3,639,572 | 2/1972 | Heinrich et al. | 424/63 |
| 3,862,809 | 1/1975 | Krochock | 424/63 |
| 3,991,184 | 11/1976 | Kludas | 424/177 |
| 4,073,881 | 2/1978 | Imai | 424/70 |
| 4,087,518 | 5/1978 | Smith | 424/70 |

FOREIGN PATENT DOCUMENTS

| | | | |
|---|---|---|---|
| 717559 | 10/1931 | France | 424/357 |
| 1073835 | 3/1954 | France | 424/357 |
| 1538342 | 7/1958 | France | 424/357 |
| 1318733 | 1/1963 | France | 424/80 |
| 1401515 | 4/1965 | France | 424/80 |

OTHER PUBLICATIONS

Miall, A New Dictionary of Chemistry, 12/1962, p. 503.
Boundy-Boyer, Styrene, Its Polymers, Copolymers & Derivatives, Reinhold Pub. 1952, pp. 678–681 & 866.

*Primary Examiner*—Dale H. Ore
*Attorney, Agent, or Firm*—Kerkam, Stowell, Kondracki & Clarke

[57] ABSTRACT

A skin firming composition comprising an aqueous solution of sodium silicate/sodium oxide mixture in a weight percent of about 14% $Na_2O$ to 33% $SiO_2$, a viscosity in centipoises of about 2,100, and a pH of about 12, a polystyrene sulfonate having an average molecular weight of about 130,000, a second water soluble polymer and, optionally, a thickening agent, and a pigment or a preservative. The method of firming human skin comprises the application of the above composition to an area of the skin and permitting the composition to dry.

13 Claims, No Drawings

SKIN FIRMING COMPOSITION AND METHOD

I. DESCRIPTION

Cross Reference to Related Application

This application is a Continuation-In-Part of Application Ser. No. 22,846, filed Mar. 22, 1979 for SKIN FIRMING COMPOSITION AND METHOD now abandoned.

BACKGROUND OF THE INVENTION

It is known to firm or smooth wrinkled human skin or skin lacking in elasticity by applying thereto one of a variety of formulations which, upon drying, operate to temporarily stretch the skin. These prior art formulations and methods, however, suffer from one or more of numerous disadvantages, namely, excessive cost, insufficient firming or smoothing action, instability, offensive odor, etc.

U.S. Pat. No. 3,862,309 describes a composition comprising an aqueous solution of from about 1% to about 5% of sodium polystyrene sulfonate having an average molecular weight of between about 300,000 and about 1,000,000, optionally containing from 0.5 to 10% of a water soluble polymer (e.g. polyvinylpyrrolidone) having an average molecular weight below about 19,000, which is particularly suited for smoothing wrinkled human skin for up to about 8 hours.

It is an object of the present invention to provide a composition and method for firming human skin lacking in elasticity which constitutes an improvement over the composition and method described in U.S. Pat. No. 3,862,309.

BRIEF SUMMARY OF INVENTION

The present invention is predicated on the discovery that an aqueous composition comprising:
(1) 0.3% to 1.0% of a 40% solution of a mixture of $SiO_2/Na_2O$ in a weight ratio of 2.4 consisting of 13.85% $Na_2O$ and 33.2% $SiO_2$, density at 68° F., °Bé of 52, a pH of 12.0, and a viscosity of 2,100.
(2) as solids, 7.5 to 15%, preferably 10.5%, of an alkali metal salt of polystyrene sulfonate having an average molecular weight of from about 10,000 to about 250,000, preferably about 130,000;
(3) as solids, 0.1 to 8%, preferably 1.5%, of a member selected from the group consisting of polyvinylpyrrolidone having an average molecular weight of from about 30,000 to about 360,000, vinylpyrrolidone-vinyl acetate copolymers (ranging from 70% vinyl pyrrolidone to 30% vinyl acetate to 30% vinyl pyrrolidone to 70% vinyl acetate) having an average molecular weight in the range of 25,000 to 35,000, vinylpyrrolidone/dimethylamino ethylmethacrylate copolymers having an average molecular weight from about 100,000 to about 1,000,000 and mixtures thereof: and,
(4) the remainder, water, said percentages being based on the weight of the composition are ideally suited for temporarily firming, tightening and smoothing human skin when applied to an area of the skin and permitted to dry.

DETAILED DESCRIPTION OF INVENTION

Historically, make-up foundations, etc., have served only two purposes, namely, to color the skin and to provide coverage for imperfections. Recently, a third purpose has been added for some make-up compositions, namely, that of moisturizing the skin. The present invention seeks not only to provide a composition and method for achieving the above objects but also to serve two additional purposes. The first of these is to firm, tighten and smooth the human skin. The second is to provide the benefits of a facial mask, namely, to refresh and stimulate the skin leaving it soft and smooth after the make-up is removed with water. The composition and method of the present invention serve to firm up those areas of the human skin to which the composition is applied and in so doing color, cover and moisturize the said area of skin without rendering the skin unnatural in appearance and leave the skin refreshed and soft after the make-up is removed.

The present invention is predicated on the discovery that in weight present, a water solution of a mixture of 13.85% $Na_2O$ and 33.2% $SiO_2$ in various combinations with specific polymers in certain critical ratios operate to temporarily firm and smooth human skin when applied thereto from an aqueous solution and allowed to dry.

A critical part of this invention is the water solution of a $SiO_2/Na_2O$ in a weight ratio of 2.4 consisting of 13.85% $Na_2O$ and 33.2% $SiO_2$, density at 68° F., °Bé of 52, a pH of 12.0, and a viscosity of 2,100. A 40% solution of the $SiO_2/Na_2O$ mixture is present in the overall composition in an amount from about 0.3% to about 1.0% by weight. The use in the composition of mixtures of $SiO_2/Na_2O$ of different weight ratios and of different densities will not result in a satisfactory product.

The alkali metal salt of polystyrene sulfonate having an average molecular weight of about 130,000 is a critical component of the composition. The amount of polystyrene sulfonate salt employed is also critical to the practice of the invention. The polystyrene sulfonate salt is most readily admixed with the remainder of the ingredients of the composition in aqueous form, preferably aqueous solutions containing about 30%, by weight, of polystyrene sulfonate, alkali metal salt. It has been found that the polystyrene sulfonate, alkali metal salt must be present in the overall composition in an amount of from about 7.5% to about 15%, by weight. Since amounts below the lower limit produce only a slight firming effect and amounts above the upper limit give rise to an uncomfortable tightening effect, it is preferred to utilize about 10.5%, by weight, of the polymer in the skin smoothing composition.

It is also critical that the composition contain from 0.1 to about 8%, preferably about 1.8% of a member selected from the group consisting of polyvinylpyrrolidone, vinyl pyrrolidone-vinyl acetate copolymers, vinylpyrrolidone/dimethylaminoethylmethyacrylate copolymers, the said polymers having the molecular weights set forth above.

It is preferred to employ about 1.5% of polyvinylpyrrolidone having a molecular weight of from about 30,000 to about 360,000, preferably 360,000, and 0.3% or less of a vinyl-pyrrolidone/dimethylaminoethylmethacrylate copolymer having an average molecular weight of from 100,000 to 1,000,000.

The most preferred combination is one utilizing 10.5% of the above-described polystyrene sulfonate salt and 1.5% of the second polymer component. Where two polymers are employed as the second polymer component, the preferred amount is 1.8%.

As the proportion or molecular weight of the polymeric components is increased, the smoothing and firming action of the resultant composition on the skin is increased proportionately. However, when the optimum ratios expressed above are exceeded, the resulting film cracks with facial movements creating an unattractive and unnatural appearing make-up. Conversely, where the proportions or molecular weights of the polymeric components are decreased below the lower limit set forth above, the resultant composition fails to produce a significant tightening or smoothing effect on the skin.

For example, the utilization of polystyrene sulfonate salts of the molecular weights set forth in U.S. Pat. No. 3,862,309, i.e., 300,000 to 1,000,000, give rise to compositions which produce brittle, unnatural films upon application to skin in the amounts set forth in this application.

In the composition, the mixture of $SiO_2/Na_2O$ in the amount of from about 0.3% to about 1.0% by weight has been found to:

1. Contribute to the tightness of the film;
2. Contribute to the durability of the film; and
3. Substantially eliminate the need for such additives as protein, propylene glycol, and similar ingredients which are used to eliminate any dry or flaky appearance of the make-up.

The composition may be applied to an area of the human skin according to any conventional manner. It is preferred, however, that the composition be applied to a clean skin free of any oil residue utilizing the finger tips. It is important that only a thin layer of the composition be applied and that it be homogenously applied over the area treated and rubbed well into the skin. Since the composition dries more quickly than traditional make-up compositions, one-half of the face should be made up at a time. In order to achieve maximum firming and smoothing the person treated should keep his or her face or skin area immobile until the applied film has hardened completely, a time requiring about three to five minutes.

The compositions described herein have been applied to various areas of the skin of numerous human subjects and animals. No evidence of toxicity, irritation or allergic reaction has been observed.

Other materials may be added to the composition as follows:

The addition of a thickening agent in the composition improves the slip as well as the viscosity of the product. The thickening agent may be added in an amount from about 0.1% to about 2%. The preferred thickening agent is magnesium aluminum silicate. Additional thickeners include cellulose gum (carboxymethyl cellulose), hydroxyethylcellulose, polyacrylic acid. Generally, any thickening agent commonly used in cosmetic and personal care formulations may be used in the composition of the invention.

Any suitable coloring agent or pigment may be added to the composition such as iron oxide pigments, titanium dioxide, talc, kaolin, zinc oxide, etc. It is preferred that the amount of coloring agent or pigment be kept in the range of from about 2 to about 12%.

A variety of water soluble preservatives may be added to the composition to improve the shelf life thereof. Suitable preservatives include potassium sorbate, imidazolidinyl urea, p-hydroxy benzoate, etc. Esters of p-hydroxybenzoic acid, CTFA designation parabens, may also be used.

There may also be included SDA alcohols to enhance the drying of the film and to aid in the preservation of the formulation.

It will be apparent to those skilled in the art that one or more of the above-mentioned additives may be omitted from the formula without materially affecting the skin firming action of the composition. Thus, if the sole purpose of the composition is to achieve skin tightening it is only necessary that the formulation contain the polystyrene sulfonate salt, the additional polymer component and water.

However, if the formulation is also to serve as make-up skin colorant, foundation, moisturizer, etc., sodium silicate, preservative, and pigments must also be included.

For example, women with naturally high color who desire only a light "sheen" coupled with skin firming action, the pigments and/or colorants may be omitted entirely.

Unless indicated to the contrary, all percentages recited herein are based on the total weight of the compositions.

The invention will be illustrated by the following non-limiting example containing the following ingredients:

| Ingredients | % |
| --- | --- |
| Deionized Water | 82.38 |
| Polystyrene sulfonate, sodium salt (average molecular weight 130,000) | 10.5 |
| Titanium dioxide (water soluble) | 3.6 |
| Polyvinylpyrrolidone (molecular weight 360,000) | 1.5 |
| Iron oxide pigments | 0.9 |
| Sodium silicate, sodium oxide mixture (Wt. Ratio ($SiO_2/Na_2O$) = 2.4, Bé. 52.0°) 40% solution | 0.8 |
| Magnesium aluminum silicate | 0.3 |
| Methylparaben | q.s. |

Fifteen percent of the deionized water was reserved and the remainder heated in a stainless steel beaker with methylparaben until the paraben dissolved. The heated water was transferred to a high shear mixer to which the magnesium aluminum silicate was added. The mixture was blended for 10 minutes at high shear speed. The sodium silicate was added and mixing continued at high speed for an additional 3 minutes. The mix was cooled to room temperature.

To the reserved 15% of the water was added the polyvinylpyrrolidone and stirred with slow stirring until all solids went into solution. The resulting solution was added slowly with moderately rapid stirring to the polystyrene sulfonate. This mixture was stirred for five minutes. The solution of water, silicate and paraben was added with stirring for an additional five minutes.

The mixture was returned to the blender to which the titanium dioxide and pigments were added.

The resulting solution was applied to the clean, oil-free face of a subject having inelastic skin and numerous wrinkles by application with the finger tips to impart a thin layer thereover which was rubbed well into the skin. After 5 minutes, the composition dried giving rise to a firm, smooth-looking skin having a natural, well-colored appearance which lasted for hours. When the make-up was removed with water, the skin felt refreshed and stimulated and was soft and smooth to the touch.

STATEMENT OF INDUSTRIAL APPLICATION

Human skin may be temporarily firmed by applying to an area of the skin a composition consisting of sodium silicate/sodium oxide mixture in a weight percent of 13.85% $Na_2O$ to 33.2% $SiO_2$, a viscosity in centipoises of about 2,100, and a pH of about 12, a polystyrene sulfonate having an average molecular weight of about 130,000, a second water soluble polymer and, optionally, a thickening agent, and a pigment or a preservative, and permitting the composition to dry.

I claim:

1. A composition adapted for temporarily firming human skin consisting essentially of:
   (1) 7.5 to 15% of an alkali metal salt of polystyrene sulfonate having a molecular weight of from about 10,000 to about 250,000;
   (2) 0.1 to 8% of a second water soluble polymer selected from the group consisting of polyvinylpyrrolidone, vinyl pyrrolidone-vinyl acetate copolymers, vinylpyrrolidone/dimethylaminoethylmethacrylate copolymers and mixtures thereof;
   (3) 0.3 to 1.0% of a 40% solution of a sodium silicate/sodium oxide mixture, in the weight ratio of 2.4 consisting of, by weight, 13.85% $Na_2O$ and 33.2% $SiO_2$ having a density at 68° F. of Baume 52.0° a pH of 12.0, and a viscosity of 2,100 centipoises; and
   (4) the remainder, water, said percentages being based on the weight of the composition.

2. The composition of claim 1 wherein said member is polyvinylpyrrolidone having a molecular weight between about 30,000 and about 360,000.

3. The composition of claim 1 wherein said member is vinylpyrrolidone/dimethylaminoethylmethacrylate having a molecular weight of about 1,000,000.

4. The composition of claim 1 additionally containing not more than 2.0% of thickening agents.

5. The composition of claim 1 additionally containing from about 2 to about 12% of a pigment.

6. The composition of claim 1 additionally containing a preservative.

7. A composition adapted for temporarily firming human skin consisting essentially of:
   (1) 10.5% sodium polystyrene sulfonate having a molecular weight of about 130,000;
   (2) 1.5% polyvinylpyrrolidone having a molecular weight of about 360,000;
   (3) 0.3% vinylpyrrolidone/dimethylaminoethylmethacrylate copolymer having a molecular weight of about 1,000,000;
   (4) 0.8% of a 40% solution of a sodium silicate/sodium oxide mixture, in the weight ratio of 2.4 consisting of, by weight, 13.85% $Na_2O$ and 33.2% $SiO_2$ having a density at 68° F. of Baumé 52.0°;
   (5) 0.3% magnesium aluminum silicate;
   (6) 3.6% titanium dioxide pigment;
   (7) 0.9% iron oxide pigment;
   (8) 0.2% of methylparaben; and
   (9) the remainder, water, said percentages being based on the weight of the composition.

8. A method for temporarily firming human skin comprising applying to an area of skin a layer of the composition of claim 1 and permitting the layer to dry.

9. A method for temporarily firming human skin comprising applying to an area of skin a layer of the composition of claim 4 and permitting the layer to dry.

10. A method for temporarily firming human skin comprising applying to an area of skin a layer of the composition of claim 5 and permitting the layer to dry.

11. A method for temporarily firming human skin comprising applying to an area of skin a layer of the composition of claim 6 and permitting the layer to dry.

12. A method for temporarily firming human skin comprising applying to an area of skin a layer of the composition of claim 7 and permitting the layer to dry.

13. A method for temporarily firming human skin comprising applying to an area of skin a layer of the composition of claim 7 and permitting the layer to dry.

* * * * *